United States Patent [19]

Guittard et al.

[11] Patent Number: 4,615,698
[45] Date of Patent: Oct. 7, 1986

[54] TOTAL AGENT OSMOTIC DELIVERY SYSTEM

[75] Inventors: George V. Guittard, Cupertino; Patrick S. L. Wong, Hayward; Felix Theeuwes, Los Altos, all of Calif.

[73] Assignee: ALZA Corporation, Palo Alto, Calif.

[21] Appl. No.: 593,024

[22] Filed: Mar. 23, 1984

[51] Int. Cl.$^4$ ............................................. A61M 31/00
[52] U.S. Cl. .................................... 604/892; 604/897; 424/15; 424/19; 424/21
[58] Field of Search ............................ 424/15, 19, 21; 604/892, 897

[56] References Cited

U.S. PATENT DOCUMENTS

| 2,648,609 | 8/1953 | Wurster | 99/166 |
| 2,799,241 | 7/1957 | Wurster | 188/24 |
| 3,845,770 | 11/1974 | Theeuwes et al. | 128/260 |
| 3,916,899 | 11/1975 | Theeuwes et al. | 128/260 |
| 4,016,880 | 4/1977 | Theeuwes et al. | 128/260 |
| 4,160,020 | 7/1979 | Ayer et al. | 424/15 |

Primary Examiner—John Kight
Assistant Examiner—M. L. Moore
Attorney, Agent, or Firm—Paul L. Sabatine; Edward L. Mandell; Steven F. Stone

[57] ABSTRACT

An osmotic device is disclosed for delivering a beneficial agent formulation to the stomach and small intestine. The device delivers substantially all of the beneficial agent in the stomach and small intestine, collapses and is easily eliminated from a host.

18 Claims, 6 Drawing Figures

TOTAL AGENT OSMOTIC DELIVERY SYSTEM

FIELD OF THE INVENTION

This invention pertains to an osmotic delivery system. The osmotic system provides a preprogrammed, unattended delivery of substantially the total amount of a beneficial agent to a preselected agent receptor. The osmotic system delivers the beneficial agent until near exhaustion of the agent from the system whereupon the system collapses and as it collapses it concommitantly delivers the remainder of the agen from the system.

BACKGROUND OF THE INVENTION

Osmotic systems manufactured in the form of an osmotic device for the administration of a beneficial agent are known in- U.S. Pat. Nos. 3,845,770 and 3,916,899 both issued to inventors Felix Theeuwes and Takeru Higuchi, and in U.S. Pat. No. 4,016,880 issued to patentees Felix Theeuwes and Nalinkant Damani. The osmotic systems disclosed in these patents are made of a thick semipermeable wall that surrounds a compartment containing a beneficial drug. The semipermeable wall is permeable to the passage of an external fluid, and it is substantially impermeable to the passage of drug. The osmotic systems have a passageway through the semipermeable wall for delivering the drug from the osmotic system. The osmotic systems are designed and manufactured with a thick wall that is substantially nonexpandable and inflexible in the presence of a beneficial agent and fluids found in the environment of use. These prior art osmotic systems are extraordinarily effective for delivering a beneficial agent that dissolves in fluid imbibed into the compartment and forms a true solution that is hydrodynamically delivered from the system. The osmotic systems are ideally suited for extended gastrointestional therapy, because they continuously deliver a drug during the prolonged time the system travels through the entire length of the gastrointestional tract. More particularly, these osmotic systems have a practical value in gastrointestional therapy as they deliver a drug beginning with their entrance into the stomach and continuously throughout the gastrointestional tract until they exit the tract through the anus.

The above discussed osmotic systems represented an outstanding and pioneering advancement in the delivery art, and they are useful for dispensing a drug throughout the entire environment of the gastrointestional tract. Now, it has been discovered a need exists for an osmotic delivery system that preferably delivers a drug in preselected regions of the gastrointestional tract, mainly the stomach and the small intestine. The need exists, because certain drugs are absorbed from these preferred regions, the stomach and the small intestine.

Moreover, there are instances when it is contraindicated to deliver a drug in a certain region of the gastrointestional tract, for example, the large intestine including the colon. The delivery of a drug in the large intestine often is contraindicated particularly, when the drug unwantingly alters the floral pattern of the large intestine. It will be appreciated by those versed in the delivery art, that if a novel and useful osmotic system were provided for delivering a drug substantially in the stomach and small intestine, such an osmotic system would have a definite use, represent an unexpected advancement and substantial contribution to the art, and have a positive value in the fields of medicine and allied therapies.

OBJECTS OF THE INVENTION

Accordingly, in view of the above presentation, it is an immediate object of this invention to provide a novel and useful osmotic delivery system that satisfies the critical need associated with the prior art.

Another object of the invention is to provide an osmotic delivery system for delivering a beneficial agent to selected agent receptor environments while substantially avoiding delivery of the agent to nonselected environments.

Another object of the invention is to provide a novel and unique osmotic system that delivers a beneficial agent until near exhaustion of the agent from the system, followed by the system collapsing and delivering substantially the remainder of the agent.

Another object of this invention is to provide an osmotic system comprising a delivery profile embodying substantially total agent delivery to a selected biological region in a time period corresponding to the time the system is in the selected region.

Another object of the invention is to provide an osmotic system shaped, sized, structured and adapted for the controlled and continuous delivery of a beneficial drug in the stomach and in the small intestine.

Another object of the invention is to provide a osmotic system comprising a semipermeable flexible wall and containin a beneficial agent that forms a viscous fluid in the presence of fluid imbibed into the system, and which wall of the system and agent cooperate with each other for delivering substantially all the agent in the stomach and small intestine.

Another object of the invention is to provide an osmotic system for dispensing a drug in the stomach and small intestine, which system during dispensing interacts with the peristaltic contraction of the stomach and small intestine, for dispensing by the combined operations of the system and the contractions, substantially all of the agent in the stomach and small intestine from the system.

Another object of the invention is to provide a collapsible osmotic system to target a antibiotic drug under controlled delivery into the stomach and the small intestine, thereby avoiding delivery into the large intestine and colon that would adversely affect the intestinal flora and lead to diarrhea.

Another object of the invention is to provide a collapsible osmotic system that becomes a shapeless collapsed mass after delivery of the beneficial agent to encourage the excretion of the osmotic system from a warm blooded animal.

Other objects, features and advantages of the invention will be more apparent to those versed in the dispensing art from the following detailed specification, taken in conjunction with th drawings and the accompanying claims.

BRIEF DESCRIPTION OF THE DRAWINGS

In the drawings, which are not drawn to scale, but are set forth to illustrate various embodiments of the invention, the drawings figures are as follows.

In the drawings and in the specification, like parts in related figures are identified by like numbers. The terms appearing earlier in the specification and in the description of the drawings, as well as embodiments thereof, are further detailed elsewhere in the disclosure.

DETAILED DESCRIPTION OF THE DRAWINGS

Figure 1:
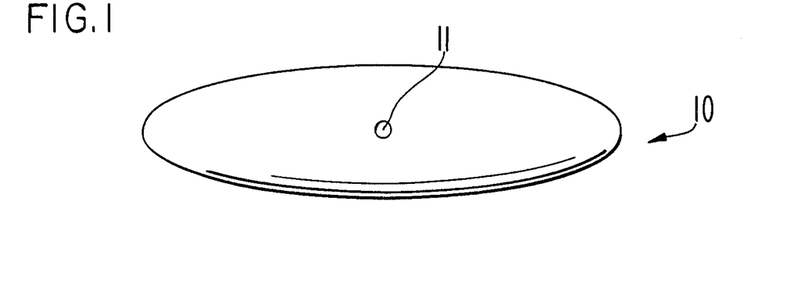
FIG. 1 is a top view of an osmotic delivery system designed and manufactured as an osmotic device for orally administering a beneficial therapeutic agent to the stomach and small intestine.
Figure 2:
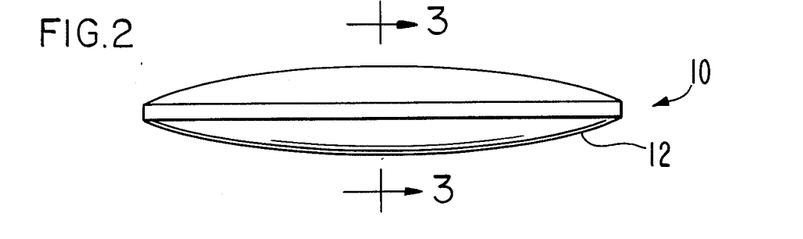
FIG. 2 is a side view of the osmotic device of FIG. 1.

Turning now to the drawings in detail, which are examples of various osmotic systems provided by the invention, and which examples are not to be construed as limiting the invention, one embodiment of an osmotic system is seen in the accompanying FIGS. 1 and 2. In FIG. 1, osmotic system 10 is seen in top view. In FIG. 1, osmotic system 10 is manufactured as an oral, osmotic device shaped, sized, structured and adapted for easy administration and prolonged retention in the biological environment of the stomach and small intestine for the controlled delivery of a beneficial, therapeutic agent thereto. Osmotic device 10 comprises a passageway 11 for delivering a beneficial agent from osmotic device 10. FIG. 2 depicts device 10 seen in a side view comprising body 12.

Figure 3:
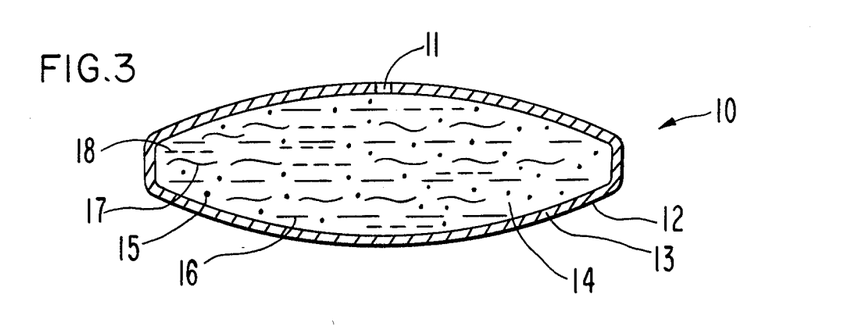
FIG. 3 is an opened view of the osmotic device of FIG. 2 through 3—3 for illustrating the structure comprising the osmotic device.

In FIG. 3, osmotic device 10 is seen in opened-section through 3—3 of FIG. 2. In FIG. 3, osmotic device 10 comprises a body 12 having a wall 13 that surrounds and forms a compartment 14. A passageway 11 in wall 13 connects compartment 14 with the exterior of device 10. Wall 13 is formed of a semipermeable polymeric composition that is permeable to the passage of an exterior fluid present in the environment of use, and it is substantially impermeable to the passage of drugs and osmotically effective agents. Wall 13 is substantially inert as it does not substantially dissolve or erode in fluids present in the environment of use. Wall 13 is formed of a semipermeable polymeric composition that is nontoxic to a host and it does not adversely affect the drug or an osmotically active agent. Wall 13 of device 10 is flexible and collapsible in the environment of use, mainly when device 10 is in operation with the collapsing occurring near or at the terminus of the drug deliver period. Compartment 14 houses a beneficial drug 15, represented by dots, that is soluble in an external fluid 16, represented by dashes, that is imbibed through semipermeable wall 13 into compartment 14, which soluble drug 15 exhibits an osmotic pressure gradient across wall 13 against an external fluid. Compartment 14 optionally contains an osmotically effective solute 17, represented by wavy lines, that is soluble in fluid imbibed into compartment 14 and it exhibits an osmotic pressur gradient across semipermeable wall 13.

Figure 4A:
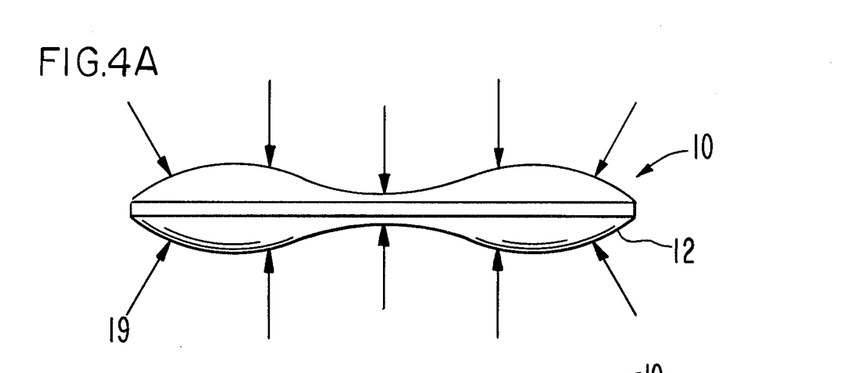
FIG. 4(A) is a side view of the osmotic device of FIG. 2 depicting the device in a collapsed state at the end of its delivery period.
Figure 4B:
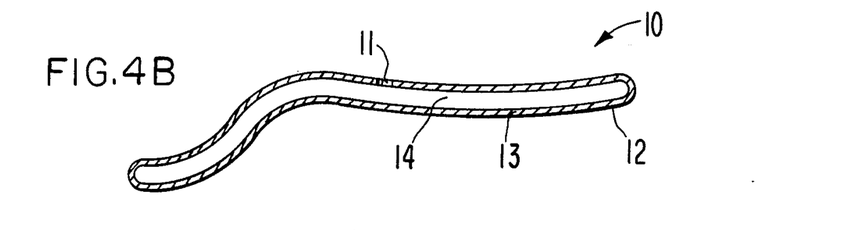
FIG. 4(B) is a side opened section view of a collapsed, shapeless osmotic system that dispensed all of its agent and is in a shape for easy excretion through the anus; and, FIG. 5 is a graph depicting the relationship between structure and properties of a series of osmotic devices.

Compartment 14 also optionally contains a viscosity inducing agent 18, represented by the broken lines. Viscosity inducing agent 18 acts by increasing the viscous property of the solution formed in compartment 14 and by decreasing its resistance to flow, thereby providing temporary internal support for wall 13. Viscosity inducing agent 18 assist wall 13 in temporarily keeping its shape, or forming a convexed shaped, until near the end of the delivery period. At this time, substantially the total amount of beneficial agent 16 and viscosity inducing agent 18 are hydrostatically pumped from device 10 accompanied by device 10 substantially collapsing in the environment of use and concomittantly exhibiting a concaved shape FIG. 4(A) and 4(B) depicts osmotic device 10 at the end of the drug delivery period. In operation, osmotic device 10 of FIGS. 1 through 4(A)(B) inclusive, manufactured in the form of an osmotic tablet, and on orally entering the gastrointestinal tract, mainly into the stomach, imbibes external fluid from the stomach through semipermeable wall 13 into compartment 14. The fluid is imbibed through semipermeable wall 13 into compartment 14 in a tendency towards osmotic equilibrium at a rate determined by the permeability of semipermeable wall 13 and the osmotic pressure gradient across semipermeable wall 13. As fluid is continually imbibed into compartment 14 it is formulated with beneficial agent 15 present in compartment 14 to increase the viscosity of the fluid which is hydrostatically pumped from osmotic device 10. Osmotic tablet 10 is fabricated with a collapsible wall. During the imbibition and formulation, the high viscosity medium formulated in compartment 14, increases the pressure inside device 10 to give device 10 a temporary hardness and convexed appearance. Device 10 dispenses agent 15 continuously through passageway 11 until substantially all of agent 15 is dispensed therefrom. Then, device 10 collapses, as seen in Figure (4A) wherein the arrows 19 indicate pressure, under the influence of applied outside gastrointestinal pressure. The combined structural, viscosity enhancing, collapsible operations of device 10 delivers substantially the total amount of agent 15 from device 10 and it substantially eliminates or reduces non-zero order tail delivery from device 10. FIG. 4(B) depicts device 10 in a totally collapsed state after delivering its beneficial agent. Collapsed device 10 are easily eliminated from the gastrointestinal tract. In FIG. 4(B) the numbers are as previously set forth.

The operation of osmotic tablet 10 is eleucidated further by the following physical presentation. That is, when the osmotic tablet is manufactured as a sphere, the burst pressure inside is a function of the stress, $\sigma$, of the membrane expressed according to equation (1) as follows:

$$P = 2 \cdot \sigma \cdot \frac{h}{r} \qquad (1)$$

wherein P is the pressure inside the osmotic sphere, h is the thickness of the wall of the osmotic sphere and r is the radius of the osmotic sphere. Further according to the example, for an osmotic sphere with a diameter of $\frac{3}{8}$ inches (9.53 mm), and a wall formed of cellulose acetate having a thickness of 2 mil (0.051 mm), with the cellulose acetate having an E=112,000 psi, Young's modulus, then $\sigma_t = 6000$ psi tensile strength.

The bursting pressure from (1) for the osmotic sphere is $P_b$ as seen in the equation (2).

$$P_b = 2 \times 6000 \times \frac{2 \times 10^{-3}}{3/16} \text{ psi} = 128 \text{ psi} \simeq 8.7 \text{ atm} \quad (2)$$

The operation pressure, $P_o$, will be small compared to $P_b$ and preferably small compared to the deformation pressure $P_d$, which may cause the flexible wall to expand slightly, usually not exceeding 10%. The pressure is obtained from equation (1) by substituting $\sigma = \epsilon E$ for $\epsilon = 1/20$ results in $P_d$ as seen in the equation (3):

$$P_d \simeq 100 \text{ psi} \simeq 7 \text{ atm} \quad (3)$$

Thus, an osmotic device 10 is manufactured with an internal pressure difference of $\Delta P = 1$ atm, the device will possess sufficient hardness to withstand the gastrointestional pressure during delivery prior to collapse.

The viscosity of the agent formulation inside the compartment of the osmotic device needed to produce the hardness for this period of time can be ascertained from Poiseuille's law set forth in equation (4):

$$\eta = \frac{\pi}{8} \cdot \Delta P \cdot \frac{r_e^4}{h} \cdot \frac{1}{V/t} \quad (4)$$

wherein $r_e$ is the radius of the passageway in the osmotic device, h is the thickness of the wall of the osmotic tablet and V /t is the fluidic volume flow from the osmotic device. Thus, when $r_e = 1$ mil, $\Delta P = 1$ atm, h = 2 mil, and V/t = 0.1 ml/hr, the viscosity is n$\simeq 10^4$ cps. Internal viscosities of this magnitude can be obtained from drug formulations, for example, from certain drugs or from a drug and viscosity inducing agent. A representative viscosity inducing agent is carboxymethylcellulose that exhibits a viscosity of 27,000 cps at a room temperature of 22° C. for a 1% weight solution of carboxymethylcellulose in 4% saline. In other embodiments, a decreased passageway and a viscous-like agent will produce a collapsible osmotic device when the internal pressure is between 1 atm and $P_d$. Additional details pertaining to the osmotic device are presented hereafter in the specification.

Osmotic device 10 of FIGS. 1 through 4, can be made into many shapes for oral use for delivering a locally acting or a systemically acting drug in the stomach and small intesting over a prolonged period of time. The device can have a conventional oral administrable shape, such as oval, sphere, convexed, oblong and the like. The device can be shaped like a capsule having a range of sizes from triple zero and from 1 to 8. In these shapes, the osmotic device can be adapted for administering drug to numerous animals. The term animal as used herein includes warm-blooded animals, which term includes mammals and humans.

While FIGS. 1 through 4(A)(B) are illustrative of various osmotic systems that can be made according to the invention, it is to be understood the systems are not to be construed as limiting, as the osmotic systems can take a wide variety of shapes, sizes and forms. The osmotic devices can be used in hospitals, veterinary clinics, nursing homes, sickrooms and the like.

DETAILED DESCRIPTION OF THE INVENTION

In accordance with the practice of this invention, it has now been found that osmotic device 10 can be manufactured with a flexible collapsible wall formed of at least one biologically acceptable wall forming material.

The selectively semipermeable materials are represented by a member selected from the group consisting of cellulose acylate, cellulose diacylate, cellulose triacylate, cellulose acetate, cellulose diacetate, cellulose ether, cellulose mono-, di-and trialtkanoates, cellulose mono-, di and triaroylates, and the like. Exemplary polymers include cellulose acetate having a D.S. up to 1 and an acetyl content up to 21%; cellulose acetate having an acetyl content of 32 to 39.8%; cellulose diacetate having a D.S. of 2 to 3 and an acetyl content of 35 to 44.8%., and the like. More specific cellulosic polymers include cellulose propionate having a D. S. of 1.8, a propionyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D.S. 2.9 to 3 such as cellulose trivalerate, cellulose trilamate, cellulose tripalmitate, cellulose trisuccinate, and cellulose trioclanoate; cellulose diacylate having a D.S. of 2.2 to 2.6, such as cellulose disuccinate, cellulose dipalmitate, cellulose dioclanoate, cellulose dipentalate, and the like.

Additional semipermeable polymers that can be used to form a sempmerable wall from 0.02 mm to 0.08 mm thick include acetaldehyde dimethylcellulose acetate, ethyl cellulose, cellulose acetate propylcarbamate; cellulose acetate phthalate for use in environments having a low ph, cellulose acetate methylcarbamate, cellulose acetate dimethylaminoacetate, semipermeable polyamides, semipermeable polyurethanes, semipermeable sulfonated polystyrenes, cross-linked selectively semipermeable polymers formed by the coprecipitation of a polyanion and a polycation as disclosed in U.S. Pat. Nos. 3,173,876; 3,276,586; 3,541,005; 3,541,006; and 3,546,142; semipermeable polymers as disclosed by Loeb and Sourirajan in U.S. Pat. No. 3,133,132; semipermeable lightly crossed-linked polystyrene derivatives; cross-linked poly(sodium styrene sulfonate); cross-linked poly(vinylbenzyltrimethyl ammonium chloride); semipermeable polymers exhibiting a fluid permeability of $10^{-5}$ to $10^{-1}$ (cc.mil/cm$^2$.hr.atm) expressed as per atmosphere of hydrostatic or osmotic pressure difference across the semipermeable wall. The polymers are known to the art in U.S. Pat. Nos. 3,845,770; 3,916,899; and 4,160,020., and in *Handbook Of Common Polymers*, by Scott, J. R. and Roff, W. J., 1971, published by CRC Press, Cleveland, Ohio.

The range of the preferred maxium and minimum thickness of a wall of an osmotic device provided by the invention can be ascertained using the following equation derived by Karman:

$$P = \frac{0.63}{1 - V^2} \left( \frac{Eh^2}{R^2} \right) \quad (5)$$

wherein V is Poisson's ratio of the membrane, E is the elastic modulus of the membrane, h is the wall thickness and R is the radius of curvature of the osmotic device manufactured as a sphere. For a wall formed of cellulose acetate, V$\simeq$0.45, which when substituted in equation (5), gives equation (6) as follows:

$$P = 0.8 \left( \frac{Eh^2}{R^2} \right) \quad (6)$$

Then substituting the pressure equation (7)

$$G = \left( \frac{Eh^2}{R^2} \right)^{\frac{1}{2}} \quad (7)$$

into equation (6), equation (8) is as follows:

$$P = 0.8 G^2 \quad (8)$$

It has been determined experimentally an osmotic system will not collapse when the collapse pressure of the wall is $G \geq 2$ (psi)$^{\frac{1}{2}}$, or $P = 165$ mmHg; and the osmotic system will collapse when the collapse pressure of the wall is less than 165 mmHg. For the osmotic systems made with a wall comprising semipermeable cellulose acetate with Young's modulus of $8(10)^4 \leq E \leq 1.4(10)^5$ psi, the mean radius of curvature for the osmotic system is $0.3 < R < 0.6$ inch (15.2 mm).

The osmotic system will collapse, when according to equations (9) and (10), $$\left( \frac{Eh^2}{R^2} \right)^{\frac{1}{2}} \leq 2(\text{psi})^{\frac{1}{2}} \quad (9)$$

$$h \leq \left( \frac{4 \cdot R^2}{E} \right)^{\frac{1}{2}} \quad (10)$$

the wall has a thickness of zero up to 3.2 mils (0.08 mm) as calculated from equation (11) as follows:

$$h \leq \left( \frac{4(0.45)^2}{8(10)^4} \right)^{\frac{1}{2}} \quad (11)$$

the wall will collapse, and when it has a thickness of greater than 3.2 mil (0.08 mm) as determined according to equation (12) the wall will not collapse:

$$h \geq \left( \frac{4 \cdot R^2}{E} \right)^{\frac{1}{2}} \quad (12)$$

The passageway of the osmotic system has a resistance to flow as ascertained by the flow rate of equation (13):

$$Q = \frac{\pi}{8} \frac{\Delta P r^4}{\eta l} \quad (13)$$

wherein is the length of the passageway, in this example 0.005 cm - 0.002 cm, r is the radius of the passageway, then the flow rate is ascertained from equation (14):

$$Q = 3(10)^{-5} \text{ ml/sec} \quad (14)$$

and $\Delta P$ the pressure drop across the passageway is expressed by equation (15):

$$\Delta P = 1(10)^6 \text{ dyne/cm}^2 = 1 \text{ atm} \quad (15)$$

which gives a viscosity expressed as poise according to equation (16):

$$\eta = \frac{\pi}{8} \frac{\Delta P r^4}{Q l} \quad (16)$$

which gives a poise as seen in equations (17) and (18) as follows:

$$\eta = \frac{\pi}{8} \frac{1(10)^6 (0.014)^4}{3(10)^{-5} (0.005)} \quad (17)$$

$$\eta = 1.0(10)^5 \text{ poise} \quad (18)$$

Thus, for the purpose of this invention the drug solution in the compartment will have a viscosity in the range of $5 \times 10^4$ to $1 \times 10^6$ poises.

The expression passageway as used herein comprises means and methods suitable for releasing the beneficial drug from the osmotic system. The expression includes aperture, orifice, bore, or hole through the semipermeable wall, or through the laminated wall. The passageway can be formed by mechancial drilling, laser drilling, or by eroding an erodible element, such as a gelatin plug, in the environment of use. The osmotic system has at least one passageway, and it can have two or more passageways. A detailed description of osmotic passageways, and the maximum and minimum dimensions for a passageway are disclosed in U.S. Pat. Nos. 3,845,770 and 3,916,899.

The osmotically effective compounds that can be used for the purpose of the invention include inorganic and organic compounds that exhibit an osmotic pressure gradient against an external fluid across the semipermeable wall or the laminated wall. The osmotically effective compounds are known also as osmotically effective solutes, osmotic agents and as osmagents. The compounds are used by mixing them with the beneficial agent that has limited solubility in the external fluid with the osmotically effective compounds forming a solution containing beneficial agent that is hydrodynamically delivered from the system. The phrase limited solubility as used herein means the beneficial drug has a solubility of about less than 1% by weight in aqueous fluid present in the environment. The osmotic solutes are used by homogeneously or heterogeneously mixing the solute with the drug, and in one manufacture charged them into the reservoir. Osmotically effective solutes used for the present purpose include magnesium sulfate, magnesium chloride, sodium chloride, lithium chloride, potassium sulfate, sodium sulfate, lithium sulfate, potassium acid phosphate, d-mannitol, urea, inositol, magnesium succinate, raffinose, sucrose, glucose, and the like.

The osmotic solute is initially present in excess and it can be in any physical forms such as particle, powder, crystal, pellet, or granular. The osmotic pressure of saturated solutions of various osmotically effective compounds and for mixtures of osmotically effective compounds at 37° C., in water, is listed in Table 1. In the table, the osmotic pressure, is in atmospheres, ATM. The osmotic pressure is measured in a commercially available osmometer that measures the vapor pressure difference between pure water and the solution to be analyzed, and according to standard thermodynamic principles, the vapor pressure ratio is converted into an osmotic pressure difference. In Table 1, osmotic pressures of from 20 ATM to 500 ATM are set forth; of course, the invention includes the use of lower osmotic pressures from zero, and higher osmotic pressures than those set forth by way of example in Table 1. The osmometer used for the present measurements is identified as, Vapor Pressure Osmometer, manufactured by Knauer Co.

TABLE 1

| COMPOUND OR MIXTURE | OSMOTIC PRESSURE @ 37° C. ATM |
|---|---|
| Lactose-Fructose | 500 |
| Dextrose-Fructose | 450 |
| Sucrose-Fructose | 430 |
| Mannitol-Fructose | 415 |
| Sodium Chloride | 356 |
| Fructose | 355 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Mannitol-Sucrose | 170 |
| Dextrose | 82 |
| Potassium Sulfate | 39 |
| Mannitol | 38 |
| Sodium Phosphate Tribasic.12H$_2$O | 36 |
| Sodium Phosphate Dibasic.7H$_2$O | 31 |
| Sodium Phosphate Dibasic.12H$_2$O | 31 |
| Sodium Phosphate Dibasic Anhydrous | 29 |
| Sodium Phosphate Monobasic.H$_2$O | 28 |

In the specification and the accompanying claims, the term beneficial drug includes any physiologically or pharmacologically active substance that produces a localized or systemic effect, or effects in animals, which term animal includes mammals, and humans. The term also includes domestic household, sport, farm, laboratory and zoo animals. The active drug that can be delivered includes inorganic and organic compounds without limitation, including drugs that act on the peripheral nerves, adrenergic receptors, cholinergic receptors, nervous system, skeletal muscles, cardiovascular, smooth muscles, blood circulatory system, synoptic sites, neuroeffector junctional sites, endocrine and hormone systems, immunological system, reproductive system, skeletal system, autocoid systems, alimentary and excretory systems, inhibitors of autocoids and histamine systems. The active drug that can be delivered for acting on these animal systems includes anti-depressants, hypnotics, sedatives, psychic energizers, tranquilizers, anti-convulsants, muscle relaxants, antiparkinson agents, analgesics, anti-inflammators, local anesthetics, muscle contractants, antibiotics, anti-microbials, anthelmintics, anti-malarials, hormonal agents, contraceptives, histamines, antihistamines, adrenergic agents, diuretics, antiscabious, anti-pedicular, anti-parasitics, anti-neoplastic agents, hypoglycemics, electrolytes, vitamins, diagnostic agents and cardiovascular drugs.

In presently preferred embodiments, the drugs are delivered by the osmotic system of this invention into the stomach and small intestine. The expression small intestine denotes the part of the intestine between the stomach and the colon consisting of the duodenum, jejunum and ileum. As examples of drugs that can be delivered and absorbed in the stomach and small intestine are folic acid, cephalosporin, cephalexin, cardiac glycosides, and the like. The beneficial drugs are known to the art in *Remington's Pharmaceutical Sciences,* 14th Ed., 1970, published by Mack Publishing Company, Easton, Pa.; and in *The Pharmacological Basis of Therapeutics,* by Goodman and Gilman, 4th Ed., 1970, published by the MacMillan Company, London.

The drug can be in various forms, such as uncharged molecules, molecular complexes, pharmacologically acceptable salts such as hydrochloride, hydrobromide, sulfate, laurylate, palmitate, phosphate, nitrite, borate, acetate, maleate, tartrate, oleate, and salicylate. For acid drugs, salts of metals, amines or organic cations, for example quaternary ammonium can be used. Derivatives of drugs such as esters, ethers and amides which have solubility characterestics suitable for use herein can be used alone or mixed with other drugs. A drug that is water insoluble can be used in a form that is a water soluble derivative thereof to effectively serve as a solute, and on its release from the device is converted by enzymes, hydrolized by body ph or other metabolic processes to the original form, or to a biologically active form. The drug can be in the reservoir compartment mixed with a binder, dispersant, wetting agent, lubricant or dye. Generally, the osmotic system will house from 0.05 ng to 5 g or more, with individual osmotic systems containing for example 25 ng, 1 mg, 5 mg, 100 mg, 125 mg, 250 mg, 500 mg, 1 g, 1.2 g, and the like. The osmotic device can be administered once, twice or thrice daily.

A drug can be in the device alone, or mixed with a viscosity inducing agent. Drugs that freely form viscous solutions with fluid imbibed into the device generally do not need the assistance of a viscosity inducing agent. Drugs that do not freely form viscous solutions with fluid imbibed into the device are preferrably present therein with a viscosity inducing agent. The viscosity inducing agent acts by increasing the viscous property of a drug solution in the device, and correspondingly decreasing its resistance to flow. The viscosity increase of the drug solution provides temporary internal support for the potentially collapsible wall of the device, until the device delivers almost all of the viscous solution, whereupon the wall reaches the collapse point and collapses. The collapse point accompanies delivery of substantially all, or all of the viscous solution, combined with the external applied pressure on the wall that forces the wall to inwardly collapse. The wall collapses under the pressure of 30 to 165 mm of Hg. The external pressure produced by the peristaltic waves of the gastrointestinal tract are about 25 to 200 mm Hg. The viscosity inducing or increasing agents presently preferred are non-ionic, water-soluble compounds that dissolve in fluid imbibed into the device and increase the viscosity of the drug solution. Representative viscosity inducing agents include polymeric cellulose derivatives such as a member selected from the group consisting essentially of alkylcellulose, hydroxyalkylcellulose hydroxyalkyl alkylcellulose, carboxyalkylcellulose, methylcellulose, hydroxymethylcellulose, hydroxypropylcellulose, hydroxypropyl methylcellulose, sodium carboxymethylcellulose, carboxymethylcellulose, and the like. The alkyl moiety of the cellulose compounds comprise from $C^1$ to $C^5$ carbons branched or straight chains. For example, a hydroxyalkyl cellulose will have from 1 to 3 carbons, and on the average of from 1 to 3 hydroxyalkyls per anhydroglucoside moiety. The viscosity average molucular weight of a hydroxyalkyl cellulose will generally be in the range of about 1 to $10 \times 10^5$. The viscosity of a 2 wt % aqueous solution generally is about 4,500 to 6,500 cps.

For polyethylene oxide with a molecule weight between 10,000 to $7(10)^6$, for a 2% solution, the viscosity is generally between 5 to 20,000 centiposes at room temperature of 23° C. For polyvinyl pyrolidone with a molecular weight between 10,000 to 500,000, for a 10% solution, the viscosity is generally between 5 to 5,000 centiposses at 25° C. For hydroxypropymethyl cellulose having a molecular weight of between 1000 to 200,000 for a 2% solution in an aqueous media the viscosity ranges is from 10 centpoises to 100,000 centpoises. For the purpose of this invention the viscosity of a viscosity building agent solution formed with an aqueous fluid imbibed into the device will be for 200 centipoises to 10,000,000 centipoises, or higher. The amount of viscosity inducing agent initially present preferably is from 0.5 to 40% of the total dry weight of all the ingredients in the compartment of the osmotic device. The viscosity of a drug solution, or the viscosity of a drug-viscosity agent inducing solution is ascertained by conventional measurements. The viscosity of a solution can be measured with a Wells-Brookfield Viscometer Model LVT, or with a Brookfield Viscometer.

The osmotic devices are manufactured by standard techniques. For example, in one manufacture the drug and other ingredients that may be housed in the compartment are mixed with a solvent into a solid or semisolid form by conventional methods such as ballmilling, calendering, stirring or rollmilling and then pressed into a preselected shape. The wall can be formed by molding, air-spraying or dipping the pressed shape into wall forming compositions. The system can be manufactured also with an empty compartment that is filled through the passageway. A presently preferred technique for forming a wall is the air suspension procedure. This procedure consists in suspending and tumbling the pressed agent in a current of air until the wall is formed surrounding the drug. The procedure is repeated with different materials to form a laminate. The air suspension procedure is described in U.S. Pat. No. 2,799,241; *J. Am. Pharm. Assoc.*, Vol. 48, pages 451 to 459, 1979; Ibid, Vol 49, pages 82 to 84, 1960; and in standard manufacturing procedures as described in *Modern Plastics Encyclopedia*, Vol. 46, pages 62 to 70, 1969., and in *Pharmaceutical Sciences*, by Remington, 14th Edition, pages 1626 to 1678, 1970, published by Mark Publishing Co., Easton, Pa.

Exemplary solvents suitable for manufacturing the wall of the laminate include inert inorganic and organic solvents that do not adversely harm the materials and the final wall or laminated wall. The solvents broadly include members selected from the group consisting of aqueous solvents, alcohols, ketones, esters, ethers, aliphatic hydrocarbons, halogenated solvents, cycloaliphatic solvents, aromatic solvents, halogenated solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, tetrachloroethane, ethyl ether, isopropyl ether, cyclohexane, cyclooctane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol.

DETAILED DESCRIPTION OF EXAMPLES

The following examples are illustrative of the present invention, and they should not be considered as limiting the scope of the invention in any way, as these examples and other equivalents thereof will become more apparent to those versed in the art in the light of the present disclosure, the drawings and the accompanying claims.

EXAMPLE 1

An osmotic delivery system manufactured as a osmotic device that is sized, shaped, structured and adapted as an osmoti tablet for orally admitting into the stomach and small intestine of the gastrointestional tract is manufactured as follows: first, 1225.50 mg of cephalexin hydrochloride is passed through a 40 mesh screen and placed into a blender. Next, 25.53 mg of poly(vinylpyrrolidone) is added to a granulating solution comprising methanol-isopropyl alcohol, 50/50, blend, and then slowly added with constant stirring to cephalexin hydrochloride in the blender. The wet blend is removed from the blender and then passed through a 16 mesh stainless steel screen. The wet granules then are dried at 50° C. for 18 hours and passed through a 16 mesh screen. Next, 25.53 mg of magnesium stearate is added to the dry ingredients in the blender, and the ingredients blended for about 5 to 10 minutes. Next, the cephalexin hydrochloride poly(vinylpyrrolidone) magnesium stearate composition is charged into the cavity of a tablet press, and a compression force of about 1.5 tons applied across a punch-head to compress the composition. The composition is compressed into a ⅞ inch, 22 mm, oval shaped drug core.

The compressed drug cores next are coated with a wall-forming composition. The composition comprises 87.0% cellulose acetate having an acetyl content of 39.8%, 6.5% of poly(ethyleneglycol) 4000, and 6.5% of hydroxypropylmethylcellulose. The cores are coated with 3% of solids in a methylene chloride - 95% ethanol solvent, 80 parts to 20 parts. A Wurster air suspension coater or Accela-Cota pan coater is used to form a semipermeable wall around the drug reservoir. After coating, residual solvent is removed by evaporating in a circulating air oven at 50° C. for 65 hours, and then after cooling to room temperature a 0.25 mm to 0.36 mm diameter passageway is laser drilled through the semipermeable wall that is 0.057 mm thick. The passageway connects the exterior of the osmotic device with the drug compartment for releasing the drug. The osmotic system delivers 95% of the cephalexin hydrochloride in 8 hours and collapses to 95% of its original volume.

EXAMPLE 2

An osmotic device is manufactured for delivery of the drug cephalexin hydrochloride to the stomach and small intestine by following the procedure of Example 1. In this example, the osmotic device contained into its compartment 612.75 mg of cephalexin hydrochloride equivalent to 500 mg of cephalexin base, 12.77 mg of poly(vinylpyrrolidone). The cephalexin hydrochloride exhibited an osmotic pressure of 143-163 atmospheres, a solubility of 685-766 mg/ml in water, and the viscosity of a saturated solution at 37° C. was 100,000 centipoises. The drug composition was compressed into a ¾ inch oval shaped core having a surface area of 3.71 cm$^2$. The drug core was coated with a semipermeable wall weighing 24 mg and 0.056 mm thick. The diameter of the passageway in the semipermeable wall was 0.36 mm.

The osmotic device exhibited a $t^{90}$ of 7.6 hours, a collapse pressure of 60–70 mm Hg, and it collapsed to 94% of its initial volume.

EXAMPLE 3

Figure 5:
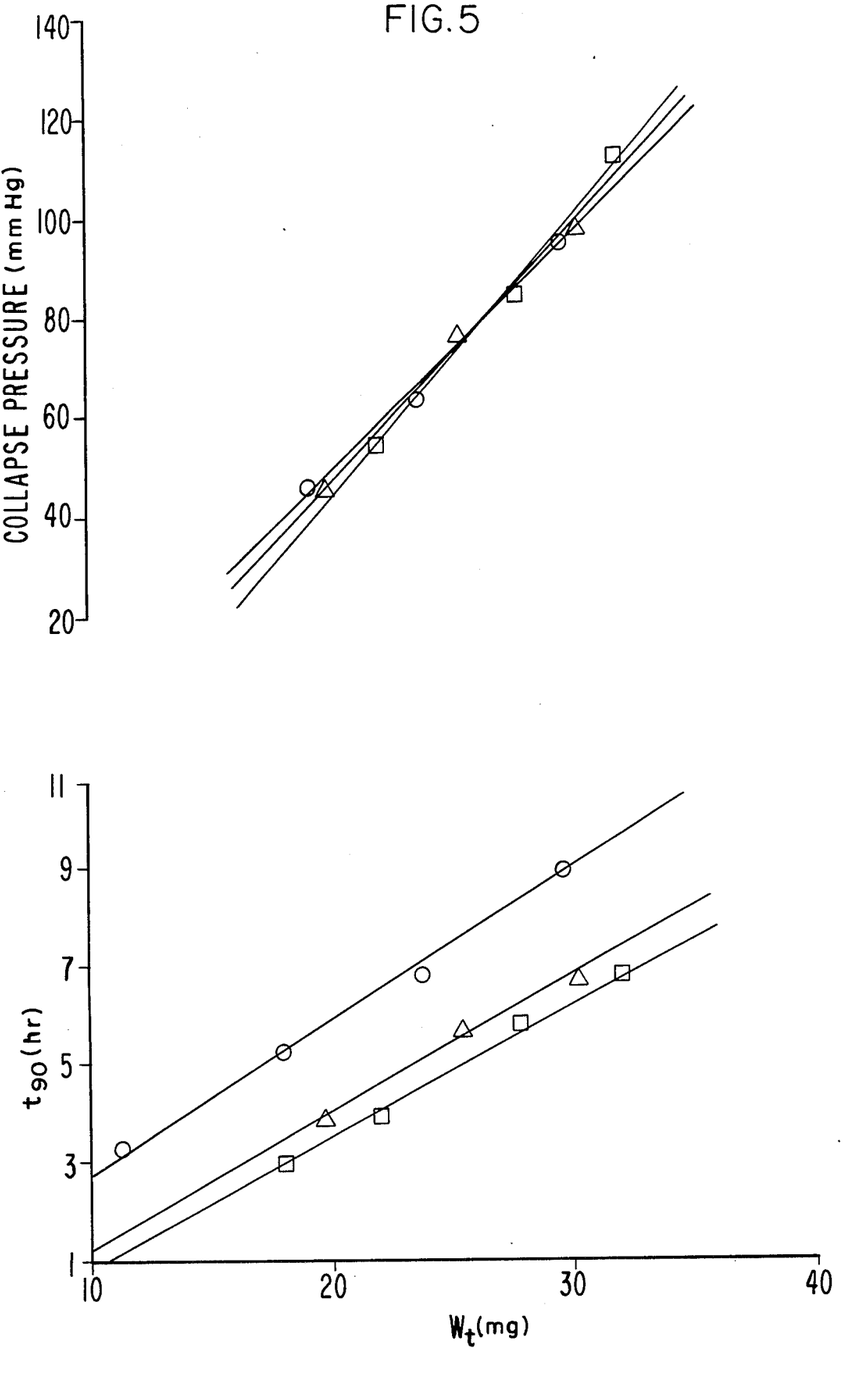

Accompanying FIG. 5 depicts the interrelationship between the structural and delivery parameters for a series of osmotic devices prepared according to the mode and manner of the invention. FIG. 5 depicts the relationship between the collapse pressure in mm Hg, the time required for delivering 90% of the drug expressed as $t^{90}$, and the total weight of the wall forming the osmotic device expressed as W'(mg) In FIG. 5, the reults expressed are for a series of osmotic devices comprising the same shape and area, and the same drug core viscosity. In FIG. 5, in the top and lower graphs, the squares indicate an osmotic collapsable device formed with a semipermeable wall comprising 80% cellulose acetate having an acetyl content of 39.8%, 10% poly(ethylene glycol) 4000 and 10% hydroxypropyl methylcellulose; the triangles represent a semipermeable walled device comprising 82% cellulose acetate having an acetyl content of 39.8%, 9% poly(ethylene glycol) 4000, and 9% hydroxypropylmethylcellulose; and, the circles represent a semipermeable wall comprising 87% cellulose acetate having an acetyl content of 39.8%; 6.5% hydroxypropylmethylcellulose, and 6.5% poly(ethylene glycol) 4000.

EXAMPLE 4

The example according to Example 2, with all conditions as described except for the addition of 20% Polyox N-80 (mw 200,000) and the orifice of the system is 0.5 mm. Other delivery systems can be prepared having a wall from 0.02 to 0.08 mm thick according to the examples.

It will be understood to those versed in the dispensing art that embodiments of this invention can be made without departing from the spirit and the scope of the invention. Accordingly, it is to be understood the invention is not to be construed as limited but embraces all equivalents inherent herein.

We claim:

1. An osmotic system for the controlled delivery of a beneficial agent formulation to an environment of use, the osmotic system comprising:
   (a) a semipermeable wall that is permeable to the passage of an external fluid, substantially impermeable to the passage of beneficial agent, and comprises at least two faced surfaces, said semipermeable wall has a maximum thickness defined by the equation $$h = \left( \frac{4 \cdot R^2}{E} \right)^{\frac{1}{2}},$$

wherein R is the radius of curvature of the osmotic system and E is the elastic modules of the wall, the wall surrounding and forming:
   (b) a compartment;
   (c) a beneficial agent formulation in the compartment that is an osmotically effective solute and exhibits an osmotic pressure gradient across the semipermeable wall against an external fluid;
   (d) at least one passageway in the semipermeable wall communicating with the exterior of the system and the compartment for dispensing agent formulation from the osmotic system; and,
   (e) wherein in operation, when the system is in the environment of use, fluid from the environment is imbibed through the semipermeable wall into the compartment forming an agent formulation solution that is dispensed through the pasageway, with the osmotic system collapsing, and the faced surfaces in close contacting arrangement at the end of the delivery period.

2. An osmotic device that delivers a beneficial drug formulation to a gastrointestinal environment and then collapses in the gastrointestinal environment, the osmotic device consisting essentially of:
   (a) an initial volume shaped, sized and adapted for easy admittance into the gastrointestinal environment;
   (b) a semipermeable collapsable wall formed of a nontoxic polymeric composition that is permeable to the passage of an external fluid, substantially impermeable to the passage of drug formulation, and wherein said wall will collapse when h is less than $$h \leq \left( \frac{4 \cdot R^2}{E} \right)^{\frac{1}{2}}$$

and will not collapse when h is larger than $$h \geq \left( \frac{4 \cdot R^2}{E} \right)^{\frac{1}{2}},$$

where R is the radius of curvature of the osmotic system and E is the elastic modules of the wall, the wall surrounding and defining;
   (c) a compartment;
   (d) a drug formulation in the compartment that is an osmotically effective solute, exhibits an osmotic pressure gradient across the semipermeable wall against fluid in the enviroment, and forms a viscous solution with fluid imbibed through the semipermeable wall into of the compartment;
   (e) at least one passageway in the semipermeable wall communicating with the exterior of the device and the compartment for dispensing drug formulation from the device; and,
   (f) wherein, when the device is in operation, fluid from the environment is imbibed through the semipermeable wall into the compartment forming a viscous solution of drug formulation that is delivered throught the passageway, with the osmotic device collapsing from 50 to 95% of its initial volume at the end of the delivery period.

3. The osmotic device for the controlled delivery of the beneficial drug formulation to a gastrointestional tract according to claim 2, wherein the viscous solution in the compartment exhibits a viscosity of from $1 \times 10^1$ to $3 \times 10^6$ centipoises.

4. The osmotic device for the controlled delivery of the beneficial drug formulation to a gastrintestional tract according to claim 2, wherein the gastrointestinal tract exhibits pressure of 25 to 200 mm Hg.

5. The osmotic device for the controlled delivery of the beneficial drug formulation to a gastrointestinal tract according to claim 2, wherein the device delivers substantially all of the beneficial drug in a prolonged period of time up to 8 hours.

6. An osmotic device adapted and dimensioned for oral admittance into a gastrointestinal tract of a warm-blooded animal, the osmotic device comprising:
   (a) a semipermeable wall formed of a pharmaceutically acceptable wall forming composition that is permeable to the passage of an external fluid, substantially impermeable to the passage of a drug formulation, and surrounds and defines;
   (b) a compartment contains a drug formulation comprising cephalexin that forms a viscous solution with fluid imbibed through the semipermeable wall into the compartment;
   (c) at least one passageway in the semipermeable wall communicating with the exterior of the device and the compartment for osmotically delivering the visoucs cephalexin solution from the device; and,
   (d) wherein, when the device is in operation in the gastrointestinal tract, fluid is imbibed through the semipermeable wall into the compartment to form the viscous cephalexin solution that is dispensed through the passageway over a period of time up to 8 hours with the device collapsing near the end of the dispensing period.

7. The osmotic device adapted and dimensioned for oral admittance into the gastrointestinal tract according to claim 6, wherein the cephalexin is cephalexin hydrochloride.

8. The osmotic device adapted and dimensioned for oral admittance into the gastrointestinal tract according to claim 6, wherein the drug formulation comprises cephalexin hydrochloride, polyvinylpyrrolidone, and magnesium stearate.

9. The osmotic device adapted and dimensioned for oral admittance into the gastrointestinal tract according to claim 6, wherein the semipermeable wall comprises cellulose acetate, polyethylene glycol and hydroxypropylmethylcellulose.

10. An osmotic device adapted and dimensioned for oral admittance into a gastrointestinal tract of a warm-blooded animal, the osmotic device comprising:
    (a) a semipermeable wall formed of a pharmaceutically acceptable wall forming composition that is permeable to the pasaage of an external fluid, substantially impermeable to the pasaage of drug formulation, and surrounds and defines:
    (b) a compartment containing a drug formulation comprising a gastrointestinal tract deliverable drug and a viscosity inducing agent that forms a viscous solution with fluid imbibed through semipermeable wall into the compartment;
    (c) at least one passageway in the semipermeable wall communicating with the exterior of the device and the compartment for delivering the drug formulation from the device; and,
    (d) wherein, when the device is in operation in the gatrointestinal tract, fluid is imbibed through the semipermeable wall into the compartment to form a viscous solution of viscosity inducing agent containing drug, that is delivered through the passageway with the device collapsing at about the end of the drug delivery period and passing from the gastrointestinal tract.

11. An osmotic device adapted and dimensioned for oral admittance into a gastrointestinal tract according to claim 10, wherein the device is structured for delivery of substantially all of the drug in a period of time up to 8 hours.

12. An osmotic device adapted and dimensioned for oral admittance into a gastrointestinal tract according to claim 10, wherein the device delivers substantially all of the drug in the stomach and small intestine of the gastrointestinal tract.

13. An osmotic device adapted and dimensioned for oral admittance into a gastrointestinal tract according to claim wherein the device is structured for delivering substantially all of the drug in a period of time up to 8 hours, and additionally structured for collapsing in a period of time up to 8 hours.

14. An osmotic device adapted and dimensioned for oral admittance into the stomach and the small intestine of a warm-blooded animal and for delivering substantially all of a beneficial agent therein, the osmotic device comprising:
    (a) a semipermeable wall formed of a pharmaceutically acceptable wall forming composition that is permeable to the passage of an external fluid is from 0.02 mm to 0.08 mm thick and collapses under a pressure of from 30 to 200 mm Hg, substantially impermeable to the passage of drug formulation, and comprises at least two faced surfaces, which wall surrounds and forms:
    (b) a compartment containing a drug formulation comprising a stomach and small intestine absorbable drug that forms a viscous solution with fluid imbibed through the semipermeable wall into the compartment;
    (c) at least one passageway in the semipermeable wall communicating with the exterior of the device and the compartment for delivering the drug formulation from the device; and,
    (d) wherein, when the osmotic device is in operation in the stomach and small intestine, fluid therefrom is imbibed through the semipermeable wall into the compartment, forming a viscous solution of drug formulation that causes the faced surfaces to convex while the drug formulation is delivered through the passageway, whereupon the convex surfaces concave at the end of the drug delivery period.

15. The osmotic system for the controlled delivery of the beneficial agent according to claim 1, wherein the beneficial agent formulation in the compartment forms a viscous solution with an external fluid imbibed into the compartment.

16. The osmotic system for the controlled delivery of the beneficial agent according to claim 1, wherein the beneficial agent formulation exhibits a viscosity of 200 centipoises to $10 \times 10^6$ centipoises in the presence of an aqueous fluid.

17. A process for enhancing the ease of elimination of an osmotic system from the gastrointestinal tract of a warm-blooded animal, wherein the process comprises providing an osmotic device that collapses in the gastrointestinal tract by the step of:
    (a) forming a beneficial agent formulation into a shape that corresponds to the initial shape of the osmotic system;
    (b) coating the formulation with a wall coating composition permeable in at least a part to the passage of fluid and substantially impermeable to the passage of beneficial agent, said wall exhibiting a maximum thickness defined by the equation $$h = \left(\frac{4 \cdot R^2}{E}\right)^{\frac{1}{2}}$$

wherein R is the radius of curvature of the osmotic system and E is the elastic modulus of the wall, and a deformation pressure less than the pressure generated in the gatrointestinal tract;

(c) forming at least one orifice in the wall that connects the exterior of the system with the formulation for dispensing the formulation to the gastrointestinal tract;

(d) admitting the osmotic system orally into the gastrointestinal tract;

(e) dispensing beneficial agent from the system by imbibing fluid from the tract into the system to form a dispensable formulation that is delivered through the orifice to the tract; and, (f) eliminating the system at the end of the end of the dispensing by collapsing the system in response to the generated pressure, thereby enhacing the ease of elmination of the system from the fastrointestinal tract.

18. A method for delivering a beneficial agent to the stomach and the small intestine of an animal, wherein the method comprises:

(1) admitting into the stomach a dispensing device, the dispensing device comprising:

(a) a semipermeable wall that is permeable to the passage of fluid, substantially impermeable to the passage of beneficial agent, and has a maximum thickness defined by the equation $$h = \left(\frac{4 \cdot R^2}{E}\right)^{\frac{1}{2}}$$

wherein R is the radius of curvature of the osmotic system and E is the elastic modulus of the wall, said wall exhibiting a collapse pressure less than the pressure generated in the stomach and in the small intestine, the wall surrounding and forming:

(b) a compartment;

(c) a beneficial agent formulation in the compartment that is an osmotically effective solute, exhibits an osmotic pressure gradient across the semipermeable wall against an external fluid, and forms a dispensable formulation with fluid imbibed into the compartment that imparts to the system a resistance against a collapsing during the delivery of formulation from the system; and, (d) a passageway in the semipermeable wall connecting the outside of the system with the compartment for dispensing agent formulation from the system;

(2) delivering the beneficial agent to the stomach and small intestine by imbibing fluid from the stomach and the small intestine into the systems to form a dispensable formulation that is delivered through the orifice to the stomach and the small intestine; and, (3) limiting the delivery of beneficial agent formulation to the stomach and small intestine by the combined operations of delivering substantially all of the beneficial agent in the stomach and small intestine and collapsing at the end of the delivery the system in response to stomach and small intestine pressure, thereby substantially maintaining delivery of the beneficial agent in the stomach and small intestine.

* * * * *